US012766342B2

(12) United States Patent
Zhang

(10) Patent No.: US 12,766,342 B2
(45) Date of Patent: Oct. 20, 2026

(54) METHODS AND SYSTEM FOR VOLUMETRIC MODULATED ARC THERAPY-COMPUTED TOMOGRAPHY (VMAT-CT)

(71) Applicant: Board of Supervisors of Louisiana State University and Agricultural and Mechanical College, Baton Rouge, LA (US)

(72) Inventor: Rui Zhang, Baton Rouge, LA (US)

(73) Assignee: Board of Supervisors of Louisiana State University and Agricultural and Mechanical College, Baton Rouge, LA (US)

( * ) Notice: Subject to any disclaimer, the term of this patent is extended or adjusted under 35 U.S.C. 154(b) by 479 days.

(21) Appl. No.: 18/541,876

(22) Filed: Dec. 15, 2023

(65) Prior Publication Data

US 2024/0198137 A1 Jun. 20, 2024

Related U.S. Application Data

(60) Provisional application No. 63/433,304, filed on Dec. 16, 2022.

(51) Int. Cl.

*A61N 5/10* (2006.01)
*G06T 12/20* (2026.01)

(52) U.S. Cl.

CPC ......... *A61N 5/1049* (2013.01); *A61N 5/1038* (2013.01); *A61N 5/1045* (2013.01);

(Continued)

(58) Field of Classification Search

CPC .. A61N 5/1049; A61N 5/1038; A61N 5/1045; A61N 5/1081; A61N 2005/1061;

(Continued)

(56) References Cited

U.S. PATENT DOCUMENTS

2009/0252292 A1* 10/2009 Simon .................. A61N 5/1071 378/65
2011/0122997 A1* 5/2011 Lu ........................ A61N 5/1042 378/65

(Continued)

OTHER PUBLICATIONS

Andersen et al. "Simultaneous algebraic reconstruction technique (SART): a superior implementation of the art algorithm", Ultrason. Imaging, (1984) vol. 6, pp. 81-94.

(Continued)

*Primary Examiner* — Kiho Kim

(74) *Attorney, Agent, or Firm* — Venable LLP; Keith G Haddaway

(57) ABSTRACT

A method for generating volumetric modulated arc therapy-computed tomography (VMAT-CT) including receiving, at a computer system comprising at least one processor, electronic portal imaging device (EPID) images collected during VMAT; performing Online Region-based Active Contour Method (ORACM) on the EPID images, resulting in binarized images; performing multi-leaf collimator (MLC) motion modeling on the binarized images, resulting in motion modeled EPID images with most of blurred regions within the EPID images removed; performing an outlier-filtering algorithm on the motion modeled EPID images, resulting in further filtered EPID images; executing a conventional FDK-based VMAT-CT reconstruction algorithm on the further filtered EPID images to provide FDK-reconstructed images; executing an iterative VMAT-CT reconstruction algorithm that combines compressed sensing and block matching and 3D filtering, on the FDK-reconstructed images, resulting in VMAT-CT images; and outputting the VMAT-CT images.

21 Claims, 11 Drawing Sheets

(52) U.S. Cl.
CPC ............ *A61N 5/1081* (2013.01); *G06T 12/20* (2026.01); *A61N 2005/1061* (2013.01); *G06T 2210/41* (2013.01); *G06T 2211/424* (2013.01)

(58) Field of Classification Search
CPC G06T 12/20; G06T 2210/41; G06T 2211/424
See application file for complete search history.

(56) References Cited

U.S. PATENT DOCUMENTS

| | | | | |
|---|---|---|---|---|
| 2012/0292534 A1* | 11/2012 | Geneser | A61N 5/1069 | 250/492.1 |
| 2013/0035587 A1* | 2/2013 | Lagendijk | A61N 5/1081 | 600/411 |
| 2013/0324784 A1* | 12/2013 | Fredriksson | A61N 5/1031 | 600/1 |
| 2015/0087879 A1* | 3/2015 | Nelms | A61B 6/5294 | 600/1 |
| 2015/0159994 A1* | 6/2015 | Hofmann | A61N 5/1049 | 356/623 |
| 2015/0265851 A1* | 9/2015 | Ma | A61N 5/1037 | 600/1 |
| 2016/0310761 A1* | 10/2016 | Li | A61B 5/0036 | |

OTHER PUBLICATIONS

Azcona et al., "Automatic prostate tracking and motion assessment in volumetric modulated arc therapy with an electronic portal imaging device", Int J Radiat Oncol Biol Phys, (2013), vol. 86, pp. 762-768.
Biguri et al., "Tigre: a Matlab-GPU toolbox for CBCT image reconstruction", Biomedical Physics & Engineering Express, (2016), 2, (11 pages).
Chan et al., "Active Contours Without Edges", IEEE Transactions on image processing, (2001), 10 266-277.
Chen et al., "A limited-angle CT reconstruction method based on anisotropic TV minimization", Phys Med Biol., (2013), 58, 2119-2141.
Cooper et al., "Real-time respiratory triggered four dimensional cone-beam CT halves imaging dose compared to conventional 4D CBCT", Phys Med Biol., (2019), 64, (13 pages), 07NT1.
Dabov et al., "Image denoising by sparse 3-D transform-domain collaborative filtering", IEEE Transactions on image processing, (2007), 16, pp. 2080-2095.
Ding et al., "Radiation Dose from Kilovoltage Cone Beam Computed Tomography in an Image-Guided Radiotherapy Procedure", International Journal of Radiation Oncology Biology Physics, (2009), 73, pp. 610-617.
Do et al., "Optimization of block-matching and 3D filtering (BM3D) algorithm in brain Spect imaging using fan beam collimator: Phantom study", Nuclear Engineering and Technology, (2022), 54, pp. 3403-3414.
Donoho "Compressed Sensing", IEEE Transactions on information theory, (2006), 52, pp. 1289-1306.
Feldkamp "Practical Cone-Beam Algorithm", J. Opt. Soc. Am. A., (1984), 1, 6, pp. 612-619.
Figueiredo "Gradient Projection for Sparse Reconstruction: Application to Compressed Sensing and Other Inverse Problems", IEEE Journal of Selected Topics in Signal Processing, (2007), 1, pp. 586-597.
Götstedt et al., "Development and evaluation of aperture?based complexity metrics using film and EPID measurements of static MLC openings", Medical physics, (2015), 42, pp. 3911-3921.
Hashemi et al., "Subband-dependent compressed sensing in local CT reconstruction", Signal, Image and Video Processing, (2015), 10, pp. 1009-1015.
Huang et al., "BM3D-based total variation algorithm for speckle removal with structure-preserving in OCT images", Appl. Opt., (2019), 58, 23, pp. 6233-6243.
Je et al., "Feasibility study for application of the compressed-sensing framework to interior computed tomography (ICT) for low-dose, high-accurate dental x-ray imaging", Radiation Physics and Chemistry, (2016), 119, pp. 272-278.
Kida et al., "4D-CBCT reconstruction using MV portal imaging during volumetric modulated arc therapy", Radiother Oncol., (2011), 100, pp. 380-385.
Kim et al., "Image quality of 4D in-treatment CBCT acquired during lung SBRT using FFF beam: a phantom study", Radiation Oncology, (2020), 15, pp. 1-13.
Kudo et al., "Image reconstruction for sparse-view CT and interior CT-introduction to compressed sensing and differentiated backprojection", Quant Imaging Med Surg., (2013), 3, pp. 147-161.
Liu et al., "Total variation-stokes strategy for sparse-view X-ray CT image reconstruction", IEEE Trans. Med. Imaging, (2013), 33, pp. 749-763.
Makinen et al., "Collaborative filtering of correlated noise: Exact transform-domain variance for improved shrinkage and patch matching", IEEE Transactions on Image Processing, (2020), 29, pp. 8339-8354.
Matsutomo et al., "Performance of compressed sensing-based iterative reconstruction for single-photon emission computed tomography from undersampled projection data: a simulation study in 123I-N-omega-fluoropropyl-2beta-carbomethoxy-3beta-(4-iodophenyl)nortropane imaging", Nucl Med Commun, (2019), 40, pp. 106-114.
McNiven et al., "A new metric for assessing IMRT modulation complexity and plan deliverability", Medical physics, (2010), 37, pp. 505-515.
Murphy et al., "The management of imaging dose during image-guided radiotherapy: report of the AAPM Task Group 75", Med Phys., (2007), 34, pp. 4041-4063.
Noh et al., "Assessment of log?based fingerprinting system of Mobius3D with Elekta linear accelerators", Journal of Applied Clinical Medical Physics, (2022), 23, (8 pages).
Noo et al., "Image reconstruction from fan-beam projections on less than a short scan", Phys. Med. Biol., (2002), 47, 2525.
Park et al., "Fast compressed sensing-based CBCT reconstruction using Barzilai-Borwein formulation for application to on-line IGRT", Med Phys., (2012), 39, 1207-1217.
Poludniowski et al., "CT reconstruction from portal images acquired during volumetric-modulated arc therapy", Phys Med Biol., (2010), 55, pp. 5635-5651.
Robar et al., "Megavoltage planar and cone?beam imaging with low?targets: Dependence of image quality improvement on beam energy and patient separation", Medical physics, (2009), 36, pp. 3955-3963.
Sheng et al., "Denoised and texture enhanced MVCT to improve soft tissue conspicuity", Medical Physics, (2014), 41, 101916, (12 pages).
Sidky et al., "Effect of the data constraint on few-view, fan-beam CT image reconstruction by TV minimization", IEEE Nuclear Science Symposium Conference Record, (2006), vol. Series 4): IEEE) pp. 2296-2298.
Sidky et al., "Image reconstruction in circular cone-beam computed tomography by constrained, total-variation minimization", Phys Med Biol., (2008), 53, pp. 4777-4807.
Sidky et al., "Convex optimization problem prototyping for image reconstruction in computed tomography with the Chambolle-Pock algorithm", Phys. Med. Biol., (2012), 57, 3065-3091.
Sidky et al., "Analysis of iterative region-of-interest image reconstruction for x-ray computed tomography", J Med Imaging (Bellingham), (2014), 1, 031007, (17 pages).
Talu "ORACM: Online region-based active contour model", Expert Systems with Applications, (2013), 40, pp. 6233-6240.
Tian et al., "Low-dose CT reconstruction via edge-preserving total variation regularization", Phys Med Biol., (2011), 56, pp. 5949-5967.
Wang et al., "Can interior tomography outperform lambda tomography? ", Proc Natl Acad Sci USA, (2010), 107, 22, pp. E93-E93.
Wu et al., "Feature constrained compressed sensing CT image reconstruction from incomplete data via robust principal component analysis of the database", Phys. Med. Biol., (2013), 58, 4047-4070.

(56) References Cited

OTHER PUBLICATIONS

Xi et al., "An Automatic Tuning Method for Camera Denoising and Sharpening based on a Perception Model", Electronic Imaging, (2018), pp. 442-1 to 442-7.
Xu et al., "Time and frequency to observe fiducial markers in MLC-modulated fields during prostate IMRT/VMAT beam delivery", Phys Med., (2020), 76, pp. 142-149.
Yao et al., "Total variation and block-matching 3D filtering-based image reconstruction for single-shot compressed ultrafast photography", Optics and Lasers in Engineering, (2021), 139, 106475, (7 pages).
Zhang et al., "Active contours with selective local or global segmentation: a new formulation and level set method", Image and Vision computing, (2010), 28, pp. 668-676.
Zhang et al., "A two-step filtering-based iterative image reconstruction method for interior tomography", J Xray Sci Technol., (2016), 24, pp. 733-747.
Zhao et al., "Feasibility of 3D tracking and adaptation of VMAT based on VMAT-CT", Radiother Oncol., (2020), 149, pp. 18-24.
Zhou et al., "Imaging Dose, Cancer Risk and Cost Analysis in Image-guided Radiotherapy of Cancers", Scientific Reports, (2018), 8, 10076, (8 pages).

* cited by examiner

METHODS AND SYSTEM FOR VOLUMETRIC MODULATED ARC THERAPY-COMPUTED TOMOGRAPHY (VMAT-CT)

CROSS REFERENCE TO RELATED APPLICATION

The present patent application claims priority benefit to U.S. Provisional Patent Application No. 63/433,304 filed on Dec. 16, 2022, the entire content of which is incorporated herein by reference.

BACKGROUND

1. Technical Field

The currently claimed embodiments of the present invention relate to volumetric modulated arc therapy-computed tomography (VMAT-CT) methods and system.

2. Discussion of Related Art

Radiotherapy (RT) is included in the treatments for more than half of all cancer patients, and it is evolving rapidly with the adoption of new technologies. Among the advanced radiotherapy (RT) techniques, volumetric modulated arc therapy (VMAT) has been increasingly used, shows specific advantages for various cancer sites, and it is expected that VMAT will eventually replace conventional intensity-modulated RT (IMRT) due to its faster delivery and improved dose conformity. However, VMAT possesses high degree of complexity and high dose gradients, so the requirement of the accurate dose delivery has increased.

Pre-treatment quality assurance and image guidance can detect certain errors, but they are not sufficient to detect intra-fractional errors or provide information on actual patient dose, and image guidance can induce extra imaging dose and treatment cost. Adaptive radiotherapy (ART) holds the potential to compensate for the errors in RT delivery and planning computed tomography (pCT), or cone beam CT (CBCT) was used for re-planning in most ART studies. However, ART based on these images cannot remedy intra-fractional errors because pCT or CBCT is only a snapshot of the patient before or after RT, and the excessive imaging dose has raised concerns. In addition, each CT scan will introduce several hundred to several thousand dollars charge (Zhou et al., 2018), which is a significant burden to the patients and the insurance system, especially when IG or ART is performed frequently. None of the current imaging techniques can provide three-dimensional (3D) or four-dimensional (4D) patient information during RT. The emerging in-treatment CBCT or magnetic resonance imaging guided linear accelerator (LINAC) has very low availability, multiple limitations, and cannot provide the 3D or 4D information without introducing substantial extra dose, elevated treatment cost, and/or treatment delay. It is highly desirable to develop a convenient, low-cost, harmless, and effective imaging tool that can catch errors, patient movement, changes in patient's anatomy, and actual patient dose during RT.

Because the daily portal images during VMAT are highly blurred due to beam modulation and commercial software cannot be used to reconstruct CT based on these images, most clinics in the US do not collect or utilize these images, to our knowledge. The huge amount of image data that do not require any additional hardware, beam time or imaging dose, could have been used for treatment monitoring and dose tracking purposes.

The concept of VMAT-CT was proposed a decade ago, which is to reconstruct three-dimensional (3D) megavoltage (MV) CT from electronic portal imaging device (EPID) images acquired during VMAT (FIG. 1). It did not gain popularity due to multiple limitations and technical challenges such as limited field of view, low image quality, lack of accurate density information.

Blurred boundaries of EPID images cause most of the artifacts in VMAT-CT. Preprocessing of EPID images before VMAT-CT reconstruction is essential.

Feldkamp, Davis, and Kress (FDK) algorithm has been used for VMAT-CT reconstruction in the original and follow-up studies. Intrinsically, the FDK-based reconstruction method suffers from distortion and artifacts due to insufficient projection data. The FDK algorithm is basically a filtered back-projection that applies a filter in the frequency domain before back-projecting the images.

BRIEF DESCRIPTION OF THE DRAWINGS

The accompanying drawings illustrate embodiments of the invention and, together with the description, serve to explain the invention. These drawings are offered by way of illustration and not by way of limitation; it is emphasized that the various features of the drawings may not be to scale.

DETAILED DESCRIPTION

Figure 1:
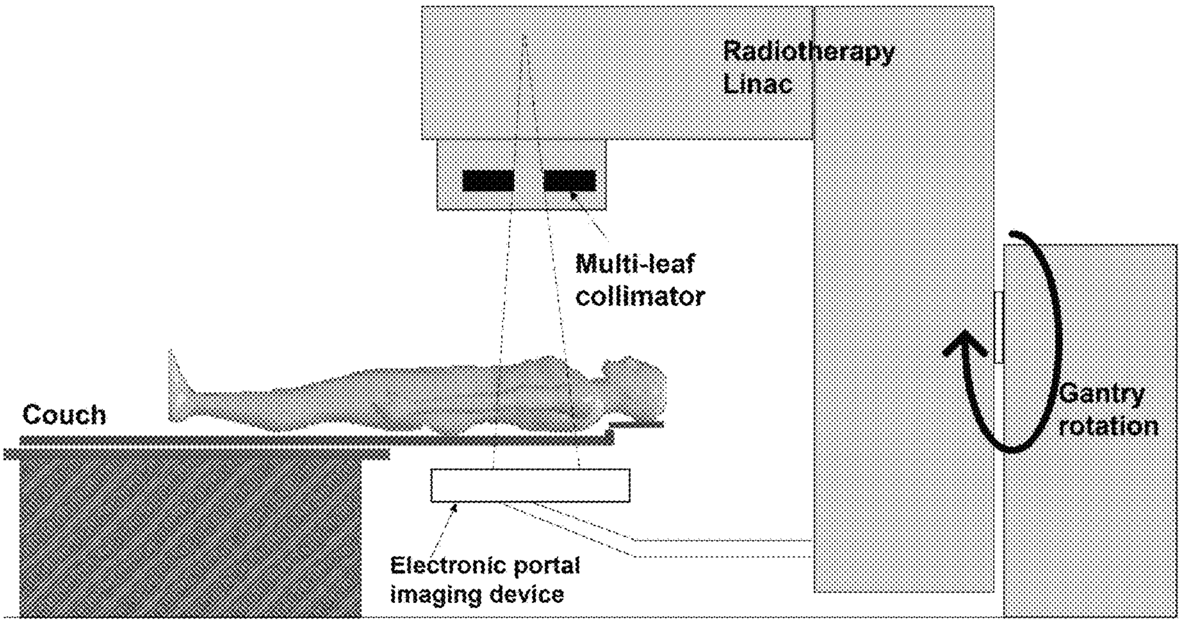
FIG. 1 is a schematic graphical representation of an exemplary linear accelerator (LINAC) geometry for VMAT.

An analytical reconstruction method based on the FDK algorithm with the lambda filter to reconstruct local tomography is employed. The generalized reconstruction formula for VMAT-CT is as follows:

$$\Lambda^m f_R(r, \varphi, z) \simeq \frac{1}{2} \frac{\Theta\left(\int_0^{2\pi} M_\beta(u', v) d\beta - \beta'\right)}{\int_0^{2\pi} M_\beta(u', v) d\beta} \int_0^{2\pi} \left[ M_\beta(u', v) \int_{-u_{max}}^{u_{max}} du D_\beta^{extrap}(u, v) e_R^{(m)}(u' - u) \right] d\beta$$

where (u, v) is the generic electronic portal imaging device (EPID) coordinate and is aligned with the panel's edge, β is the gantry angle, $e_R$(u'−u) is the convolution kernel defined by the lambda filter, Θ-function is the Heaviside step function to cut off the reconstructed data with insufficient angular coverage, and $M_\beta$(u, v) is the masking function describing the multi-leaf collimator (MLC) aperture at gantry angle β. If we defined the aperture extent in the interval [$u_1$, $u_2$] at a particular v and β, the binary masking function $M_\beta$(u, v) is defined as follows:

$$\begin{aligned} M_\beta(u, v) &= 1 \text{ if } u_1 < u < u_2(v, \beta) \\ &= 0 \text{ otherwise} \end{aligned}.$$

$$D_\beta^{extrap}(u, v)$$

is the extrapolated portal projection at the pixel (u, v) on the EPID detector at gantry angle β, with extrapolation scheme defined as follows:

$$\begin{aligned} D_\beta^{extrap}(u, v) &= D_\beta(u_1, v) \text{ if } u(v, \beta) < u_1(v, \beta) \\ &= D_\beta(u, v) \text{ if } u_1(v, \beta) < u(v, \beta) < u_2(v, \beta). \\ &= D_\beta(u_2, v) \text{ if } u(v, \beta) > u_2(v, \beta) \end{aligned}$$

This extrapolation is required for the purpose of the convolution integral because the raw projection $D_\beta$(u, v) has a very limited area.

Although VMAT-CT can potentially provide spatial information of the patient during VMAT delivery, the image quality of VMAT-CT is poor and one major cause is the blurred boundaries of EPID images due to the fast MLC movement during VMAT. The blurry regions would result in poor extrapolation of EPID images, which subsequently introduces artifacts to VMAT-CT because the image gradient of the blurry regions will be enhanced after lambda filtering and become artifacts in filtered EPID images. For the complex treatment plans with high modulation complexity score and small aperture score, the extrapolation would be especially difficult because the blurred edges of the truncated portal images would be significant due to MLC motions.

Although the lambda tomography does not require an exact and unique reconstruction of VMAT-CT, ray-sampled voxels in some VMAT delivery are extremely deficient, fewer than the lowest acceptable cut-off threshold (1.57 radians or 90°), so the failed VMAT-CT reconstructed using the original FDK-based algorithm would appear distorted and full of artifacts. To overcome the inherit limitations of FDK algorithm, iterative reconstruction algorithms should be utilized because iterative reconstruction algorithms can introduce image constraints, which can be prior known information or realistic assumptions on the missing data such as positivity of voxel values, bounds on image smoothness and voxel values, such that the CT reconstruction can be protected from unrealistic artifacts and distortions coming from data deficiency.

Systems configured as disclosed herein can utilize a combination of distinct image processing methods to improve the image quality of VMAT-CT. In some configurations, the system may only use one or more of these image processing methods. Exemplary image processing methods can include: (1) Online Region-based Active Contour Method (ORACM), to binarize portal images. (2) MLC motion modeling, to remove the MLC motion blur. (3) Outlier-filtering, to further remove blurry debris. In addition, the system can utilize a compressed sensing (CS)-based iterative reconstruction algorithm that can further improve the image quality of VMAT.

Systems configured as disclosed herein provide a clinically viable solution to daily patient positioning, in vivo dosimetry, treatment monitoring and plan adaptation. The systems can use multiple algorithms to drastically improve the image quality of VMAT-CT. This significantly increases the confidence of VMAT and ART, catches and remedies errors during treatment, allows dose escalation, and reduces radiation toxicity. It also allows daily ART without introducing additional imaging dose or cost as other image guidance techniques do, and can actually reduce them, e.g., it essentially removes the necessity of pre-treatment imaging for ART or tracking purpose and can completely replace in-treatment and post-treatment CBCT because the patient's information during RT is already recorded. The methodology developed in this study is also applicable to Tomotherapy which is another widely used rotational RT technique, dynamic arc stereotactic radiosurgery, and any other RT to be developed in the future as long as the beam is rotational and the exit radiation pattern can be recorded. While some configurations utilize Elekta LINAC, the methods are also applicable to other types of LINACs. Clinical introduction of the systems and methods disclosed herein can benefit all cancer patients in any clinic who will receive rotational RT.

FIG. 1 is a schematic graphical representation of the linear accelerator (LINAC) geometry for VMAT. The patient lies on the treatment couch, and the EPID panel is extended underneath the couch and can form images of the patient based on the exit radiation beam. The LINAC gantry together with EPID continuously rotate during VMAT, and VMAT-CT can be reconstructed based on EPID images collected during VMAT, according to an embodiment of the present invention.

Figure 2:
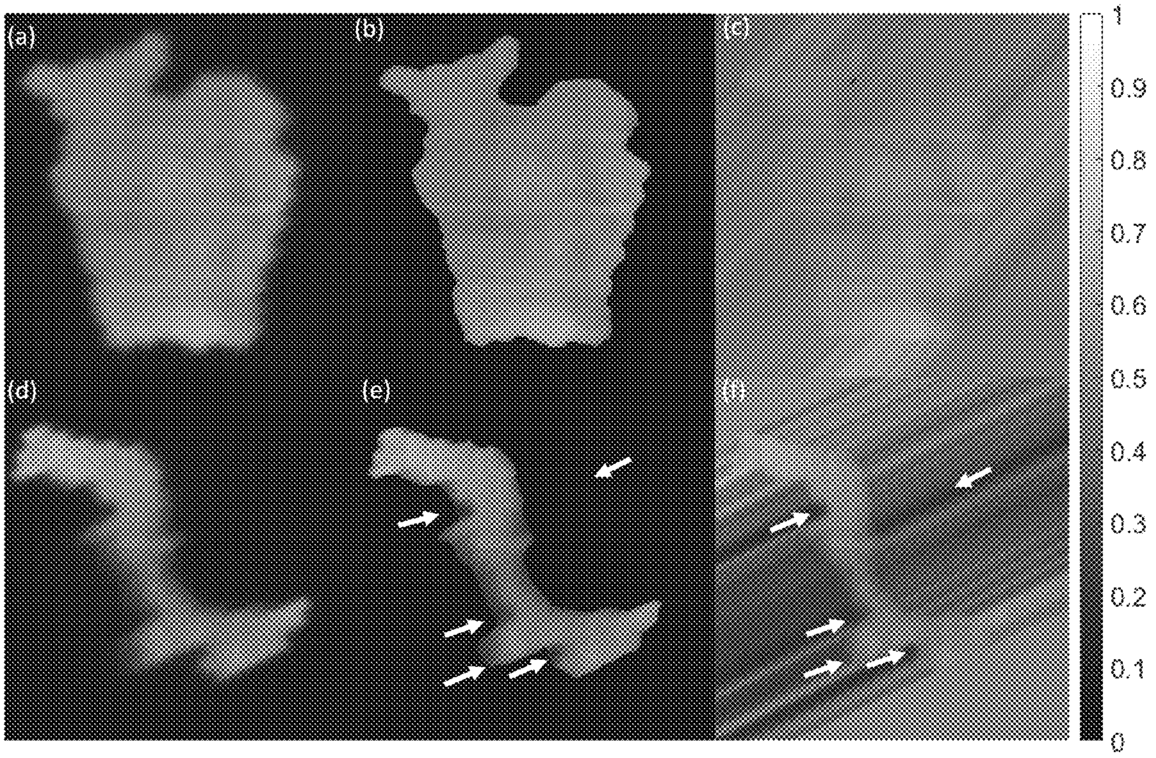
FIG. 2 demonstrates an example of morphological erosion and extrapolation of portal images.

Morphological erosion: The simplest method to remove the blurred edge of EPID images is uniform morphological erosion. This method works well for EPID images from VMAT plans with slow leaf motions because the blurred edge originated from MLC motion is negligible and can be removed effectively by a uniform erosion. This is illustrated in FIG. 2, panels (a), (b), and (c). Panel (d) illustrates examples of raw portal images from VMAT plans with slow and fast leaf motions, respectively. Panels (b), (c) show examples processed images, while panels (a) and (d) show exemplary images after uniform morphological erosion. Panels (c) and (f) show examples of extrapolated portal images based on images (b) and (c). The arrows in image (e) indicate the remaining blurry areas after morphological erosion and cause artifacts in data extrapolation, while the vertical scale grey bar helps understand the extrapolation, according to an embodiment of the present invention However, for VMAT plans with fast leaf motions, the large and irregular blur cannot be effectively removed this way and can cause artifacts in data extrapolation (FIG. 2 (d), (c), (f)).

Online Region-based active contouring (ORACM): Accurate EPID-MF can eliminate non-motion blur effectively and reduce the uncertainties when matching EPID-MF and summed MLC control points for the data alignment in MLC motion modeling. Rather than using a gradient-based thresholding method to calculate the EPID-MF (where the tuning the gradient threshold is labor-intensive, and the threshold is vulnerable to noises and local changes such as inhomogeneous exposure or streaking artifacts), the system disclosed herein uses another image segmentation method named ORACM to calculate the EPID-MF more accurately and efficiently. The ORACM is a fast image segmentation algorithm based on the region-based active contour model. The ORACM does not require extra tuning because it takes no parameters for the iteration speed, contour smoothness, or thresholding, and also evolves to the solution much faster because the ORACM doesn't calculate the gradient of the level set function, which is the computational bottleneck for the traditional active contour method.

MLC motion modeling: The system of the invention can model the MLC motion and remove the blurry edges based on the modeling. The first step can be securing data alignment between EPID data and LINAC log file. The EPID data can contain images and cumulative Monitor Units (MUs) recorded by Elekta iView® system from Elekta Solutions based in Stockholm, Sweden. The LINAC log file can contain MLC positions (X collimation), jaw positions (Y collimation), gantry angles, and cumulative MUs extracted via iCom communication from ICom Inc. using Mobius Log. For better MLC motion modeling, the data in the LINAC log file can be interpolated into higher time resolution as time intervals of 0.05 s, and the two data sets can be coarsely aligned according to the values of cumulative MUs in both data.

Figure 3:
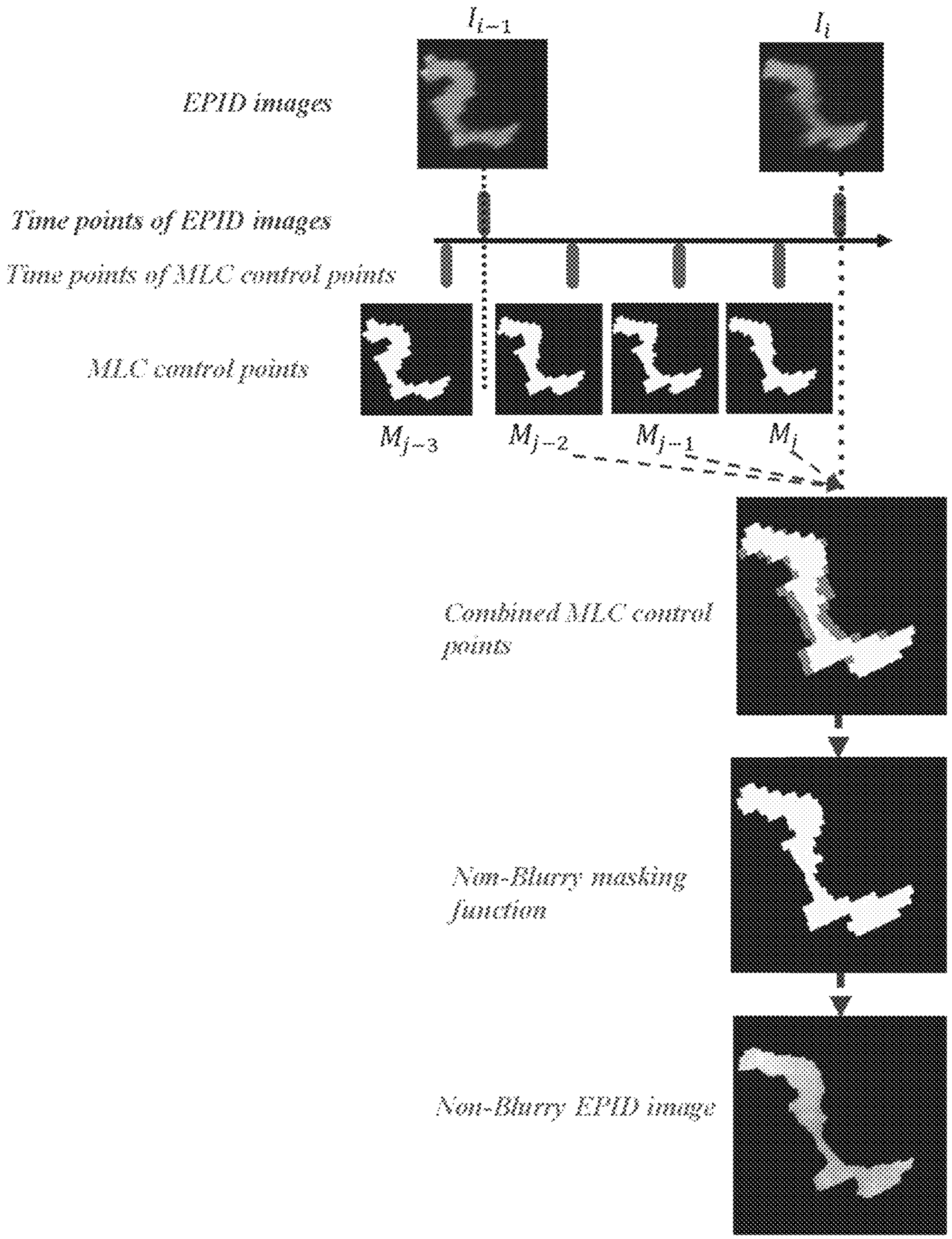
FIG. 3 is an exemplary flow diagram showing multi-leaf collimator (MLC) motion modeling to remove blurred areas in EPID images, according to an embodiment of the present invention.

The masking function for each EPID image is the summation of MLC control points within the interval between two consecutive EPID images after data alignment (FIG. 3). At this step, the system can fine-tune the synchronization based on the structural similarity index measure (SSIM) between the summed MLC control points and EPID-MF. For example, the system can slightly deviate the aligned time sequences from the previous coarse alignment by ±0.5 s (or another time period), calculating the average SSIM of all frames and finding the optimal synchronization between the two automatically based on SSIM values. The time sequence that results the highest SSIM value is the optimal one. The bright regions in the summed control points shown in FIG. 3 represent the fully exposed area on EPID without any blur. The grey regions or the blurred regions are the partial exposure area caused by the fast leaf motions and can be removed automatically by the system using the exact location of these regions per the MLC modeling.

Figure 4:
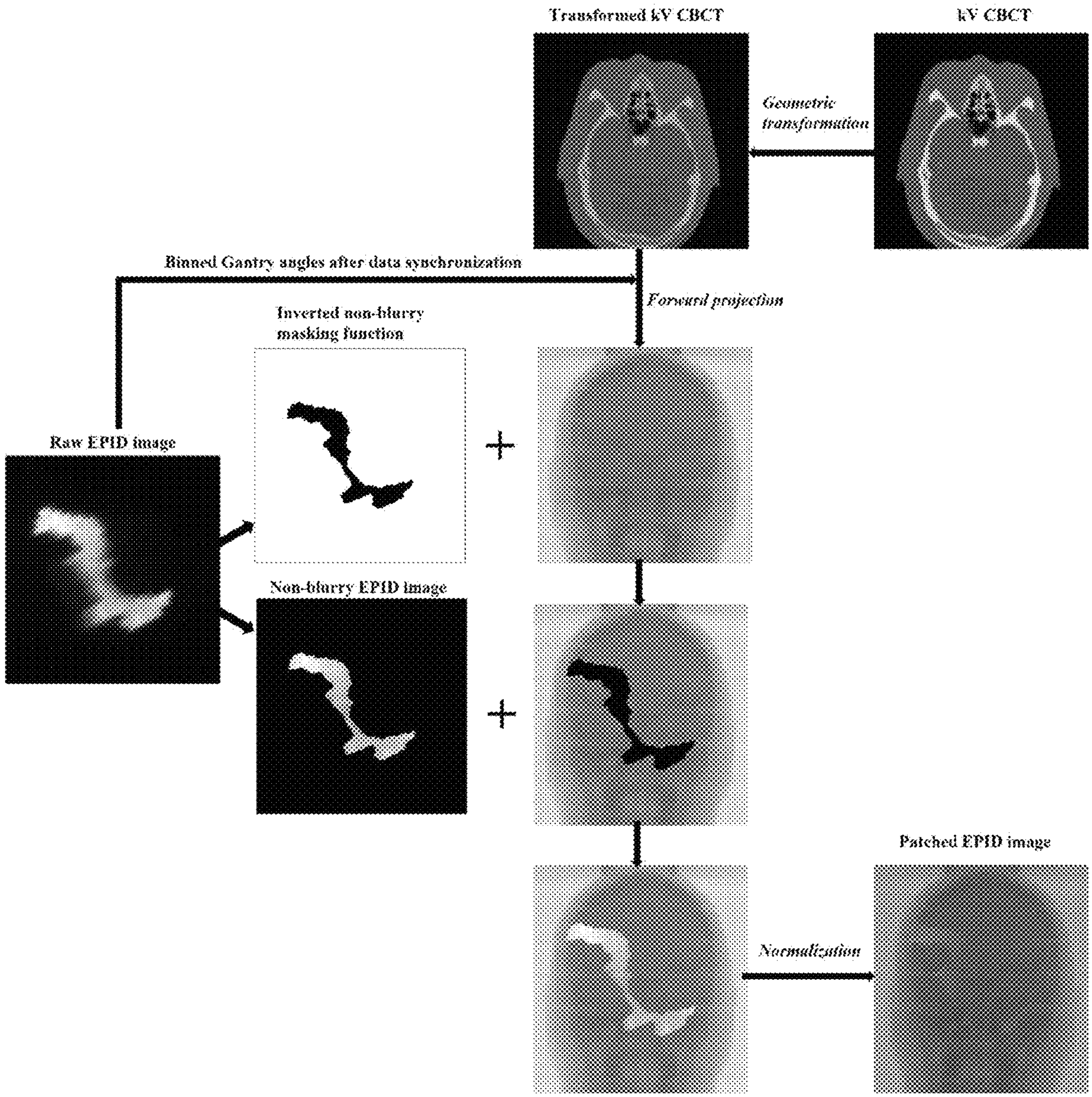
FIG. 4 is an exemplary flow diagram showing a workflow of generation of patched EPID images, according to an embodiment of the present invention.

Generation of patched EPID images and outlier-filtering: Although MLC modeling can effectively remove most of the blurred regions in EPID images, some blurry debris may remain due to the small discrepancy between the motion model and the true VMAT delivery. To further remove the debris, the system can use an extrapolation method to fast extrapolate the truncated EPID images by combining the MLC-blocked area with the raw portal image (FIG. 4). FIG. 4 shows the workflow of generation of patched EPID images. Since kV-CBCT is widely used for setup verification in most external radiotherapy, pretreatment kV-CBCT was the image set we used for this method.

First, pretreatment kV-CBCT is transformed to the image domain of VMAT-CT. To do that, the system uses open-field EPID images (e.g., 24×24 cm) of a phantom and reconstructed MV-CBCT, which is in the same image domain as VMAT-CT, using FDK CBCT reconstruction algorithm.

Second, the system registered kV-CBCT to MV-CBCT, generating a 3D rigid geometric transformation matrix between kV-CBCT and MV-CBCT. Image registration is a procedure in medical physics that transforms different sets of image data into a single coordinate system. In the present case, kV and MV data are registered to transform kV-CBCT to VMAT-CT domain. This transformation matrix can be used to transform the 3D image domain from pretreatment CBCT (or planning CT) to the VMAT-CT. Because the image quality of phantom CBCT may affect the matrix, the system can collect kV and MV CBCT of the rando phantom at different sites including head and neck, right lung, left lung, and esophagus, calculated the geometric transformation matrix for each of the sites, and assign the transformation matrix to a specific VMAT treatment plan according to the treatment site.

Third, the open-field EPID images are simulated using the transformed CBCT, the gantry angles from the log files collected during VMAT, and cone-beam forward projection operator from the TIGRE toolbox. Because the system is attempting to identify the missing data blocked by MLC, the system can calculate the masking function of the outer area, which could be done during the step of MLC modeling and overlap the outer area with simulated open-field EPID images as the outer images.

Finally, the outer images are normalized with the mean values of the pixels on the boundary of raw EPID images and then combined with the raw images as the extrapolation area (FIG. 4).

Although the simulated extra data within the patched EPID images are to be avoided in the reconstruction process since it may contain a false signal, they can provide plausible image intensity around the boundary of raw image data and enable the outlier filter to remove the remaining blurry regions precisely. Outlier-filtering can be implemented before and after the convolution of EPID image with the lambda filter: the first outlier filter can work as a crude filter to remove the remaining blurred regions after MLC modeling. Because the blur is always dimmer than the true data, the system can filter out the outliers on the lower tail of pixel intensity histogram and replace them with the mean values. After lambda filtering, the second outlier filter may take two-sided tails and smooth out the spiky signals in EPID images. Spiky signals may appear on the boundary of the filtered image due to the residual intensity discrepancy on the boundary, and the residual discrepancy may be amplified after lambda filtering, which is why a second outlier filter can be required to remove them. The filtering window for the outlier filter is 30 pixel-width (or other size as needed by a specific configuration) because the statistical outliers may be wrong if sample size is too small. Nevertheless, the filtering window may require tuning for the best outlier detections and removals depending on the MLC motion speed and complexity.

Figure 5:
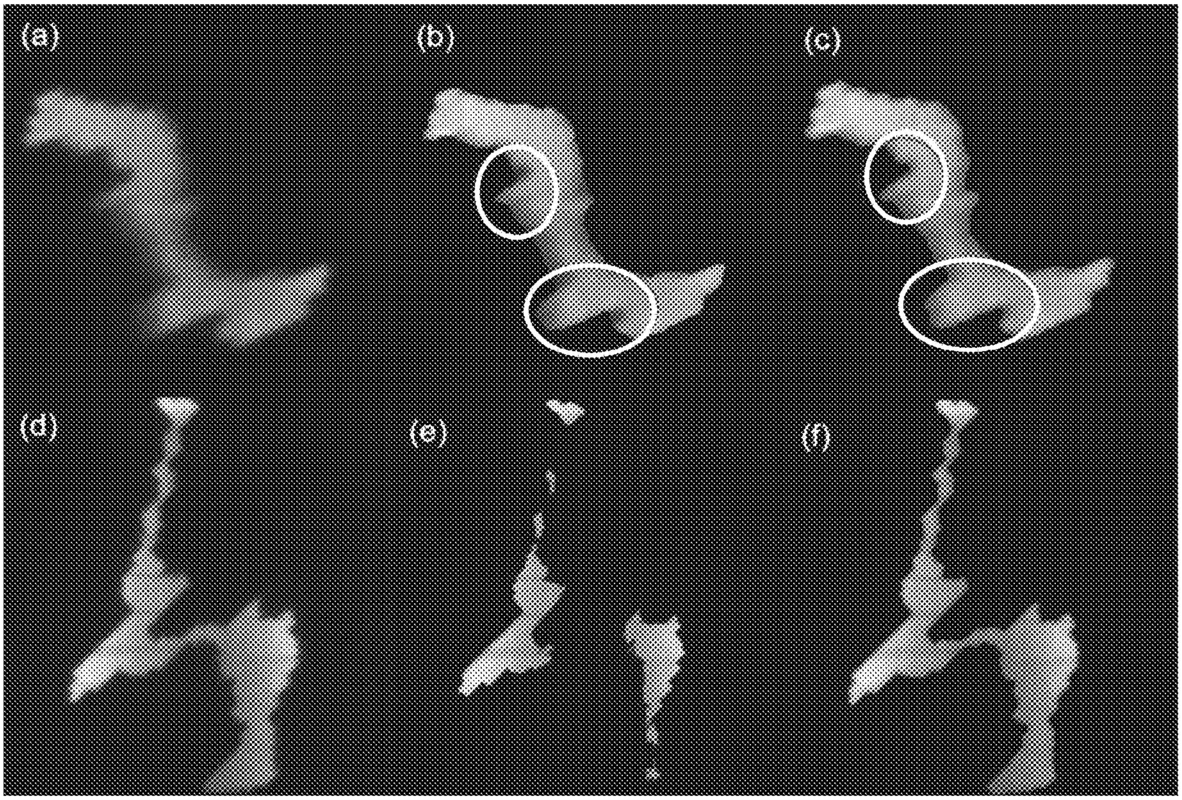
FIG. 5 shows a plurality of exemplary images demonstrating the advantages of online region-based active contour method (ORACM.

FIG. 5 shows the strengths of ORACM. Panels (a), (d) are original EPID images, panels (b), (c) are images obtained by masking function generated by gradient-based thresholding method, and panels (c), (f) are images showing masking function generated by ORACM, according to an embodiment of the present invention. The EPID-MF generated by gradient-based thresholding method (FIG. 5*b*) has obvious blurred areas, while the one generated by ORACM is free of large, blurred edges (FIG. 5*c*). Also, the gradient-based thresholding method may fail to correctly binarize an EPID image if the dynamic range of an EPID image is large (FIG. 5*c*), while ORACM is robust even for an EPID image with a large dynamic range in exposure (FIG. 5*f*). The masking function generated by gradient-based thresholding method (b) has obvious blurred areas (white circled areas), while the one generated by ORACM is free of large, blurred edges (c). The gradient-based thresholding method fails to correctly binarize an EPID image when the dynamic range of an EPID image is large and the masking function could be discontinuous and distorted (c), while ORACM is robust for this kind of EPID image (f).

Figure 6:
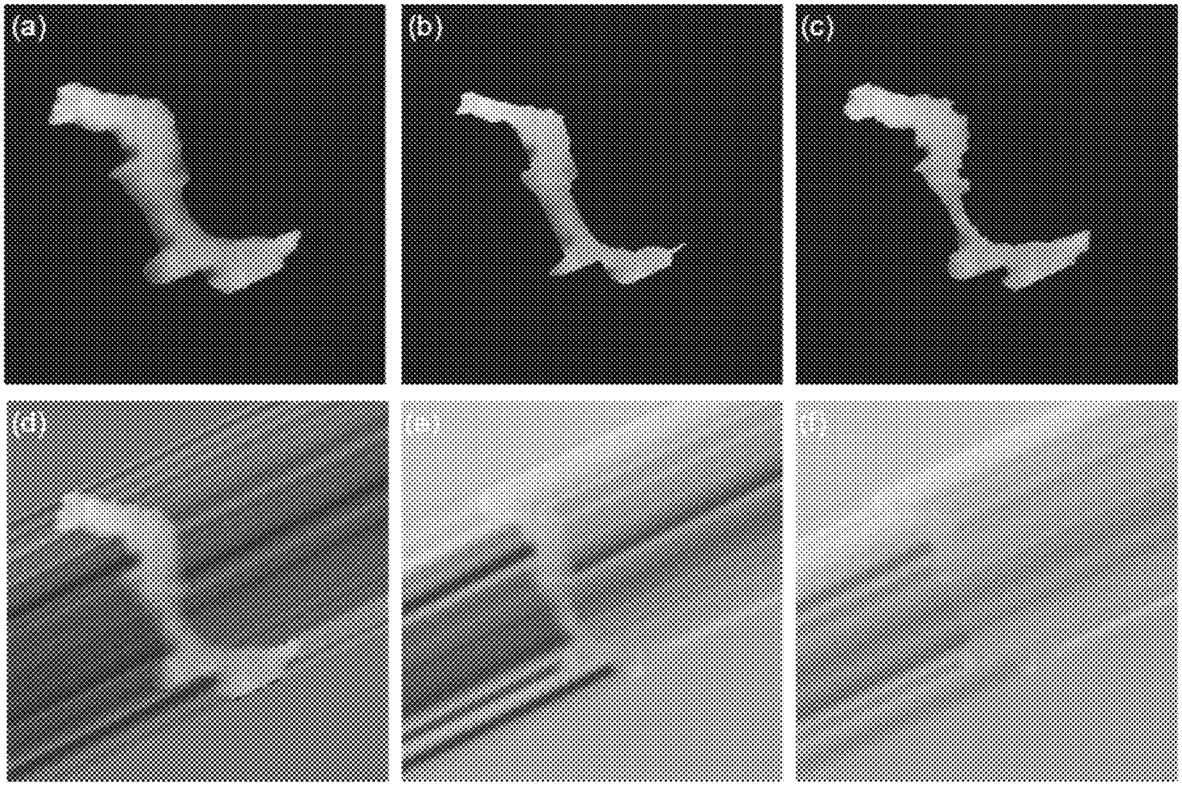
FIG. 6 shows a plurality of exemplary images demonstrating the advantages of multi-leaf collimator (MLC) modeling.

Compared with the uniform erosion method, using MLC modeling not only removes the blurred edges more effectively but also saves more true image data for VMAT-CT reconstruction, as shown in FIG. 6. In FIG. 6, panels (a), (d) show the original EPID image and its extrapolation; panels (b), (c) show the EPID image after uniform morphological erosion and its extrapolation; and panels (c), (f) show the EPID image after MLC modeling and its extrapolation, according to an embodiment of the present invention. Therefore, MLC modeling can generate more accurate masking function and reduce artifacts.

Figure 7:
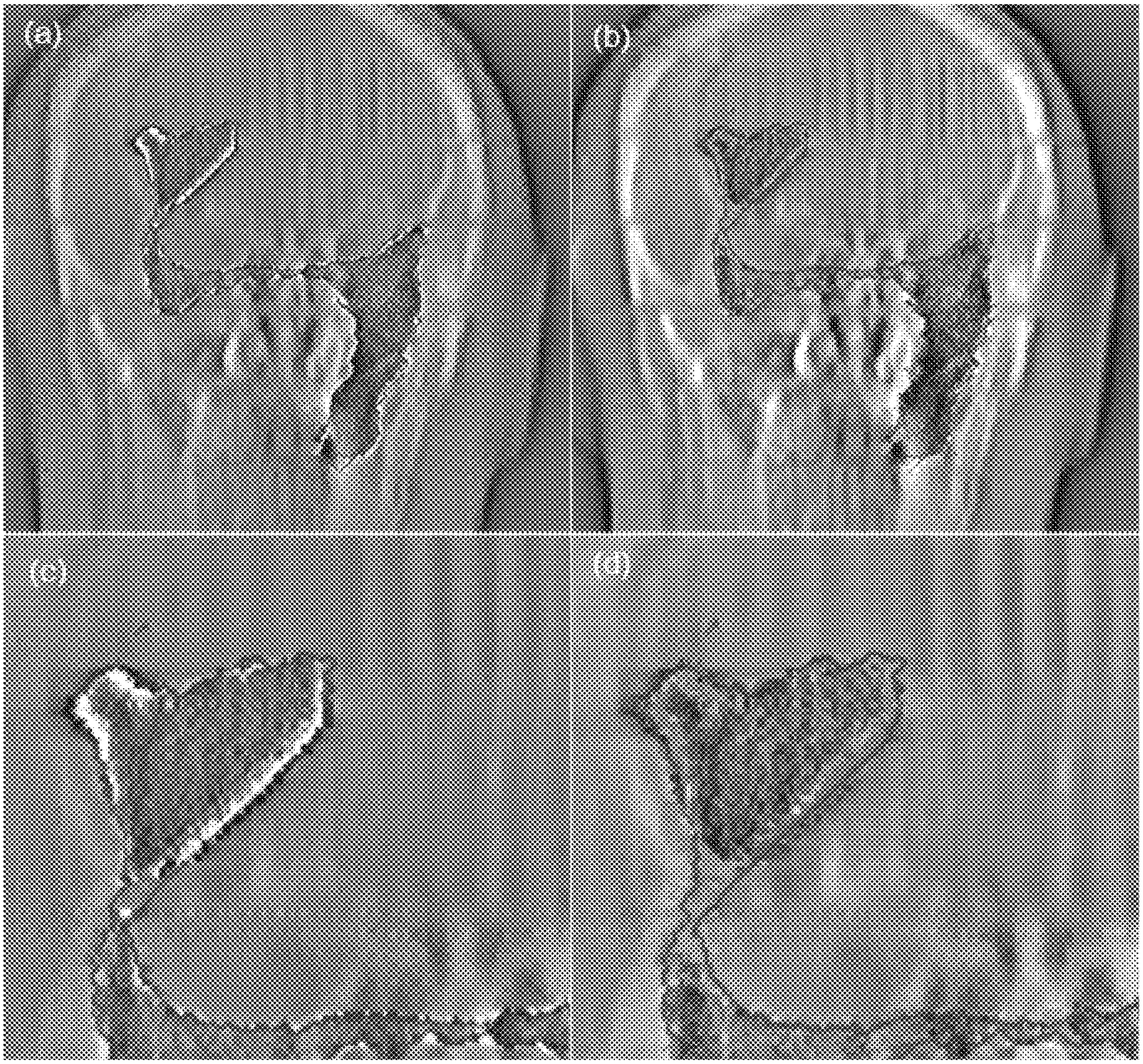
FIG. 7 shows a plurality of images demonstrating the advantages of outlier-filtering.

FIG. 7 shows a plurality of images demonstrating the advantages of outlier-filtering; panels (a), (b) show EPID images before and after outlier-filtering, while panels (c), (d) show zoomed-in version of images in panels (a) and (b), according to an embodiment of the present invention. More specifically, FIG. 7 (a) and (c) show spiky signals on the boundary of the lambda-filtered patched image. After outlier-filtering, the spiky signals are replaced by the local means. The two-stage outlier-filtering is applied to the vicinities of the boundary of each EPID image (see the perimeter of the dark object in the middle of the panels b and d), so the signals within the EPID image are protected from the potential signal pollution induced by the outlier-filtering process.

Figure 8:
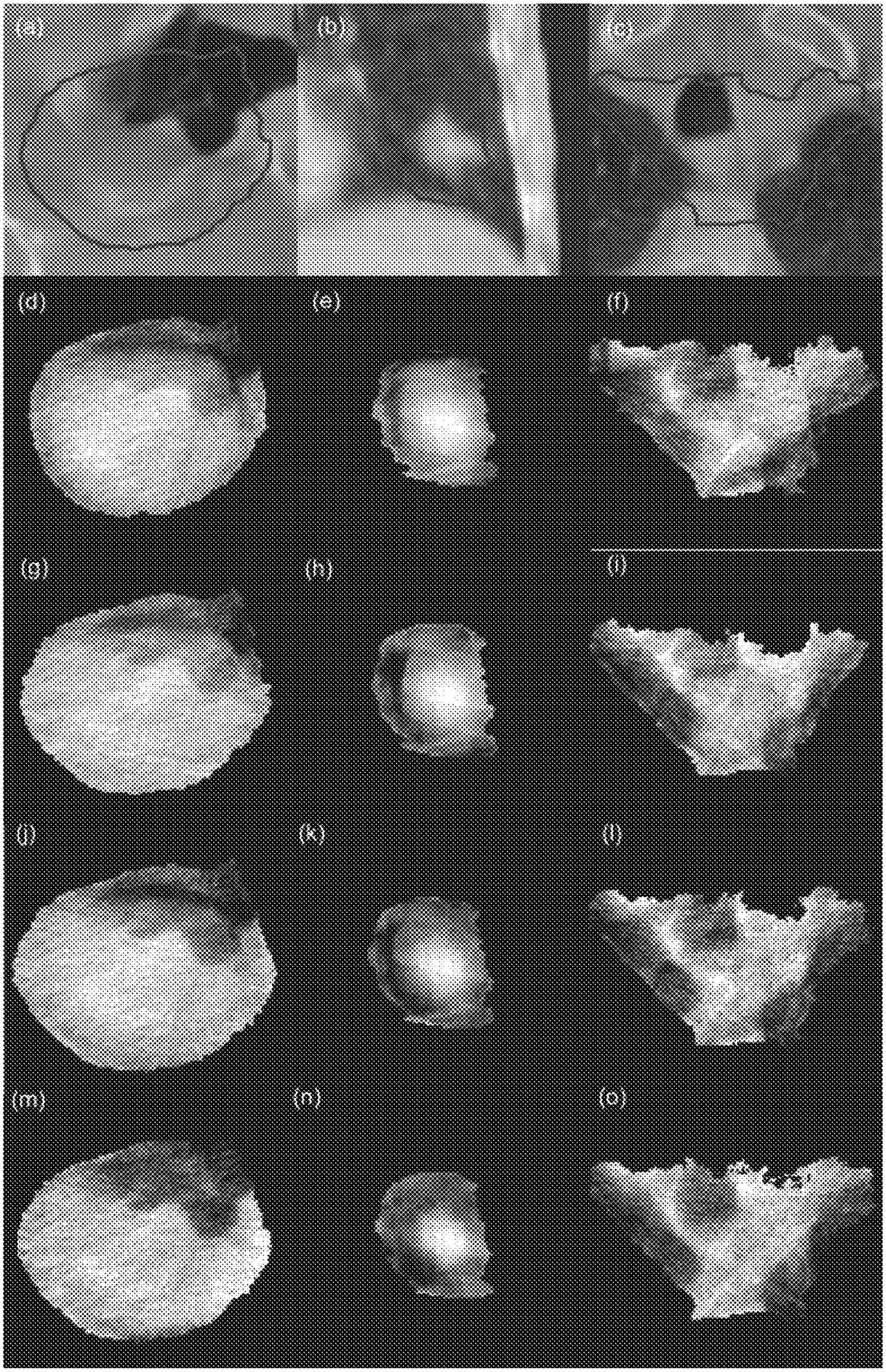
FIG. 8 shows a plurality of images depicting VMAT-CT reconstructions of real-patient cases.

The three preprocessing methods (Online Region-based Active Contour Method (ORACM), to binarize portal images, MLC motion modeling, to remove the MLC motion blur, and Outlier-filtering, to further remove blurry debris) proposed in this system can function together provide different impacts in different combinations. FIG. 8 shows a plurality of images depicting VMAT-CT reconstructions of real-patient cases with the disease in the thoracic regions. FIG. 8 has a right lung plan (first column), a left lung plan (second column), and an esophagus plan (third column). Panels (a), (b), (c) show the pretreatment CT images overlaid by the isodose lines; panels (d), (c), (f) show the original VMAT-CT reconstruction with constant extrapolation and uniform edge erosion; panels (g), (h), (i) show the VMAT-CT reconstruction with ORACM; panels (j), (k), (l) show the VMAT-CT reconstruction with ORACM and MLC motion modeling; and panels (m), (n), (o) show the VMAT-CT reconstruction with ORACM, MLC motion modeling, and outlier-filtering, according to an embodiment of the present invention. Stated another way, the first row of VMAT-CT images, which are based on the original method, i.e., EPID images were processed with constant extrapolation, uniform edge erosion, and collimator angle correction, suffered from lots of streaking artifacts. With ORACM and MLC motion modeling for the blur removal, the improvement of image quality of VMAT-CT can be easily recognized. By combining ORACM, MLC modeling, and two-stage outlier filtering together, the VMAT-CT can be further saved from distortions and artifacts caused by the unwanted signals, show better contrasts and are most comparable to the pretreatment CBCT.

Compressed Sensing (CS)-based iterative reconstruction: Iterative reconstruction algorithms for incomplete projection data have been proposed to overcome the limitations of FDK algorithm. According to CS theory, a signal can be reconstructed from fewer sampling than the number required by Nyquist sampling theorem if the signal is sparse. Consequently, if an image f can be sparsified by operations such as a discrete gradient operator, which can be represented as Ψf, the image can be reconstructed from less sampling. The Adaptive-Steepest-Descent Projection Onto Convex Sets (ASD-POCS) was proposed to incorporate the regularization term called Total Variation (TV) into CT reconstruction iterative algorithm. The TV of image f is defined as the sum of the magnitudes of its discrete gradient at every pixel or voxel. For the case of 3D CT f, the TV is written as:

$$\|\Psi f\|_1 = \|f_{i,m,n}\|_{TV} = \sum_{i,m,n} \mu_{i,m,n} = \sum_{i,m,n} \sqrt{(f_{i,m,n} - f_{i-1,m,n})^2 + (f_{i,m,n} - f_{i,m-1,n})^2 + (f_{i,m,n} - f_{i,m,n-1})^2}$$

where $\mu_{i,m,n}$ is the magnitude of its discrete gradient at voxel (i, m, n).

Block Matching and 3D filtering (BM3D): BM3D is an effective denoising approach in terms of denoising performance on images. To remove the streaking artifacts and noises in VMAT-CT, the system uses an adopted BM3D algorithm into 3D VMAT-CT. The algorithm is divided in two major steps: (1) The first step estimates the denoised image using hard thresholding during the collaborative filtering; (2) the second step is based both on the original noisy image, and on the basic estimate obtained in the first step. It uses Wiener filtering during the collaborative filtering.

This algorithm incorporated TV minimization into the process of CT reconstruction iterative algorithm and thus yielded the following constrained convex optimization problem:

$$\min_f \mathcal{F}(f) = \|Rf - p\|_2^2 + \lambda\|f\|_{TV} \text{ s.t. } f \geq 0$$

where R is the forward projection operator, p is the raw projection data, λ is the hyperparameter controlling the weight of the regularization, and $\|f\|_{TV}$ is the TV regularization term shown above and represents the sparseness constraint of CT image. The ASD-POCS algorithm treats the optimization as two phases in each iteration: the first phase is to enforce the projection data consistency, which is represented by the fidelity term $$(\|Rf - p\|_2^2),$$

using the simultaneous algebraic reconstruction technique (SART) and the non-negativity of the reconstructed CT (f); the second phase is to minimize TV with the adaptive steepest gradient descent algorithm (Sidky et al., 2006).

However, because VMAT-CT reconstruction is performed within a local volume that is much smaller than the field of view of open-field conventional CT or cone beam CT (CBCT), the projection operation Rf, which represents the Radon transform in discrete form, fails to describe the incomplete Radon transform situation of VMAT-CT. Instead, the projection operator can be modified with the local filtering operator, which would work effectively for projection data truncation. Therefore, we modified the fidelity term to be $$\|(Rf)_L - (p)_L\|_2^2$$

to relate the projection operation of VMAT-CT to the raw truncated EPID images, where L represent the local filtering. The EPID image after local filtering operation can be represented as:

$$p_L(u, v) = p(u, v) \circledast e_R(u)$$

where (u, v) is the generic electronic portal imaging device (EPID) coordinate and $e_R$ the convolution kernel defined by the local filter.

Furthermore, the BM3D regularization term besides TV regularization is incorporated into the TV-BM3D iterative algorithm. The final optimization problem could be expressed as $$\min_f \mathcal{F}(f) = \|(Rf)_L - p_L\|_2^2 + \lambda\|f\|_{TV} + \kappa\|f\|_{BM3D} \text{ s.t. } f \geq 0$$

where L denotes the local filtering, $\|f\|_{BM3D}$ is the BM3D regularization term, and κ is the hyperparameter controlling the weight of BM3D regularization.

Figure 9:
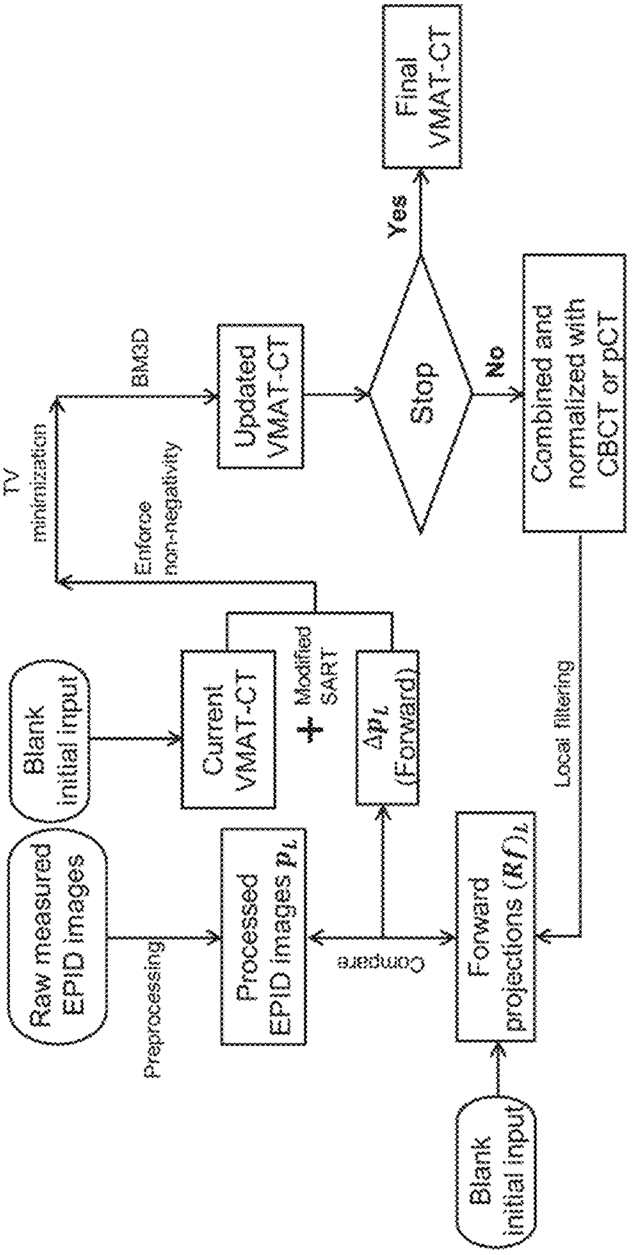
FIG. 9 is an example flow chart of iterative VMAT-CT reconstruction algorithm.

The ASD-POCS framework is modified for VMAT-CT reconstruction, as shown in FIG. 9, where SART corresponds to simultaneous algebraic reconstruction technique (SART), pCT corresponds to planning CT, Δ is a difference, TV is a total variation, BM3D corresponds to Block Matching and 3D filtering, according to an embodiment of the present invention. First, after the raw EPID data were preprocessed, the projection difference between the filtered EPID images and the locally filtered forward projections from a 3D CT input (a blank CT initially) was calculated, (i.e., $\Delta p_L = p_L - (Rf)_L$). The projection difference ($\Delta p_L$) was then back-projected to VMAT-CT domain using modified SART, and VMAT-CT (f) (a blank image set initially) was updated.

In the next regularization steps, the non-negativity of each voxel is enforced in VMAT-CT, and implemented the total variation (TV) minimization using the GPU accelerated compute unified device architecture (CUDA) code in the tomographic interactive graphical processing unit-based reconstruction (TIGRE) toolbox. Next, the BM3D denoising was performed by using the BM3D MATLAB package.

The reconstructed VMAT-CT (f) was checked with the stopping criteria: if the iteration reached the maximum iteration number ($N_{stop}$), or if the square difference of reconstructions between two successive iterations was below a predetermined threshold.

Finally, if none of the stopping criteria was met, VMAT-CT f would be normalized and combined with pretreatment CBCT or registered planning CT (pCT) and sent back for the next iteration loop.

Figure 10:
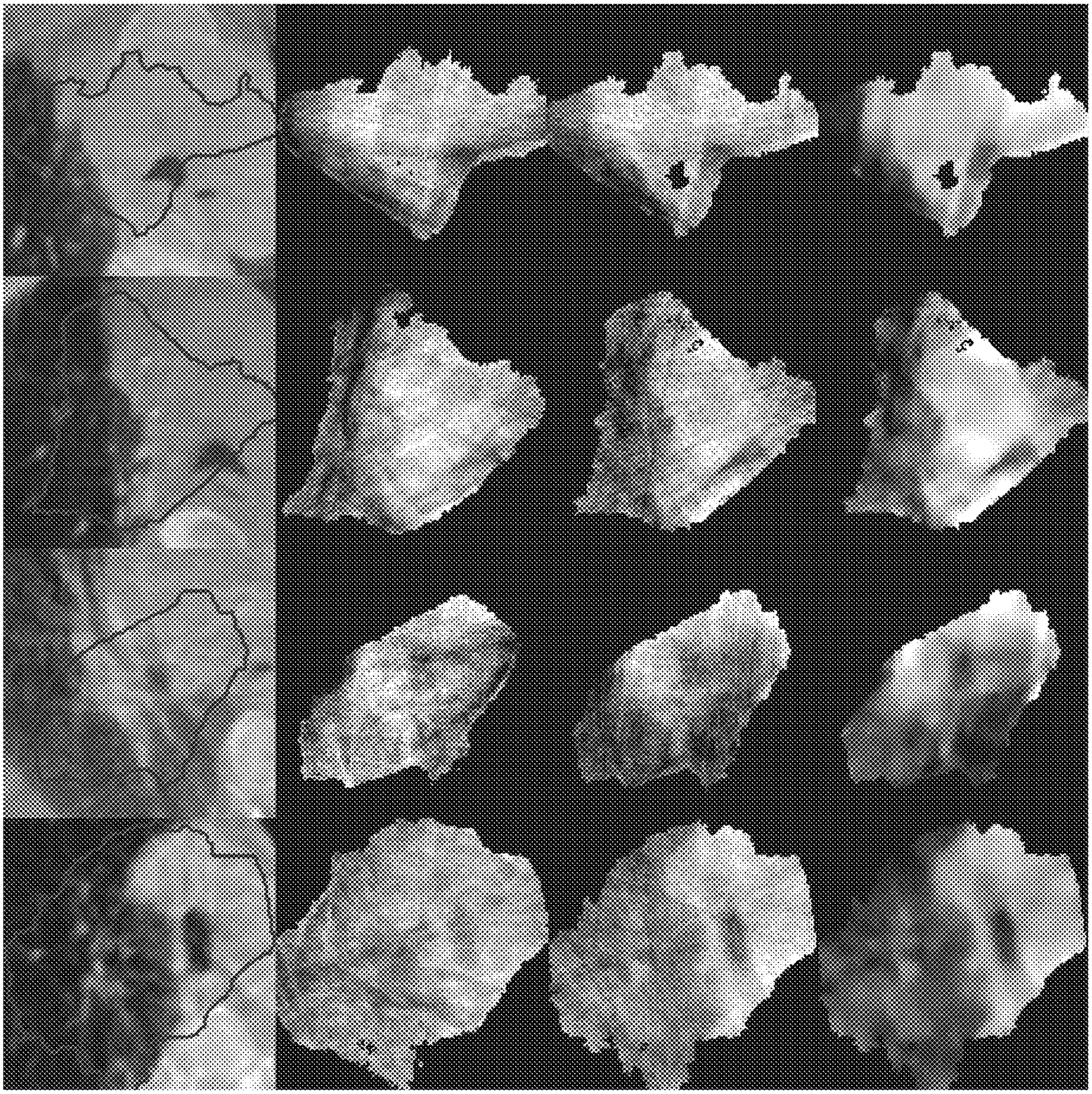
FIG. 10 shows a plurality of example images showing VMAT-CT reconstructions of real-patient cases.

FIG. 10 shows real-patient cases with the disease in the thoracic region. The first column of images correspond to the pretreatment CBCT images overlaid by the isodose lines, the second column of images correspond to the VMAT-CT reconstructed with original FDK-based analytical method, the third column of images corresponds to the VMAT-CT reconstructed by original FDK-based method together with the combined preprocessing method, and the fourth column of images correspond to the VMAT-CT reconstructed by the iterative algorithm together with the combined preprocessing method, according to embodiments of the present invention The VMAT-CT images based on the original FDK reconstruction method suffer from many streaking artifacts. The VMAT-CT images reconstructed with the original VMAT-CT reconstruction method together with the preprocessing method have limited improvements. The VMAT-CT images reconstructed with the TV-BM3D iterative reconstruction method have further improved image quality and discernable anatomy structures.

Figure 11:
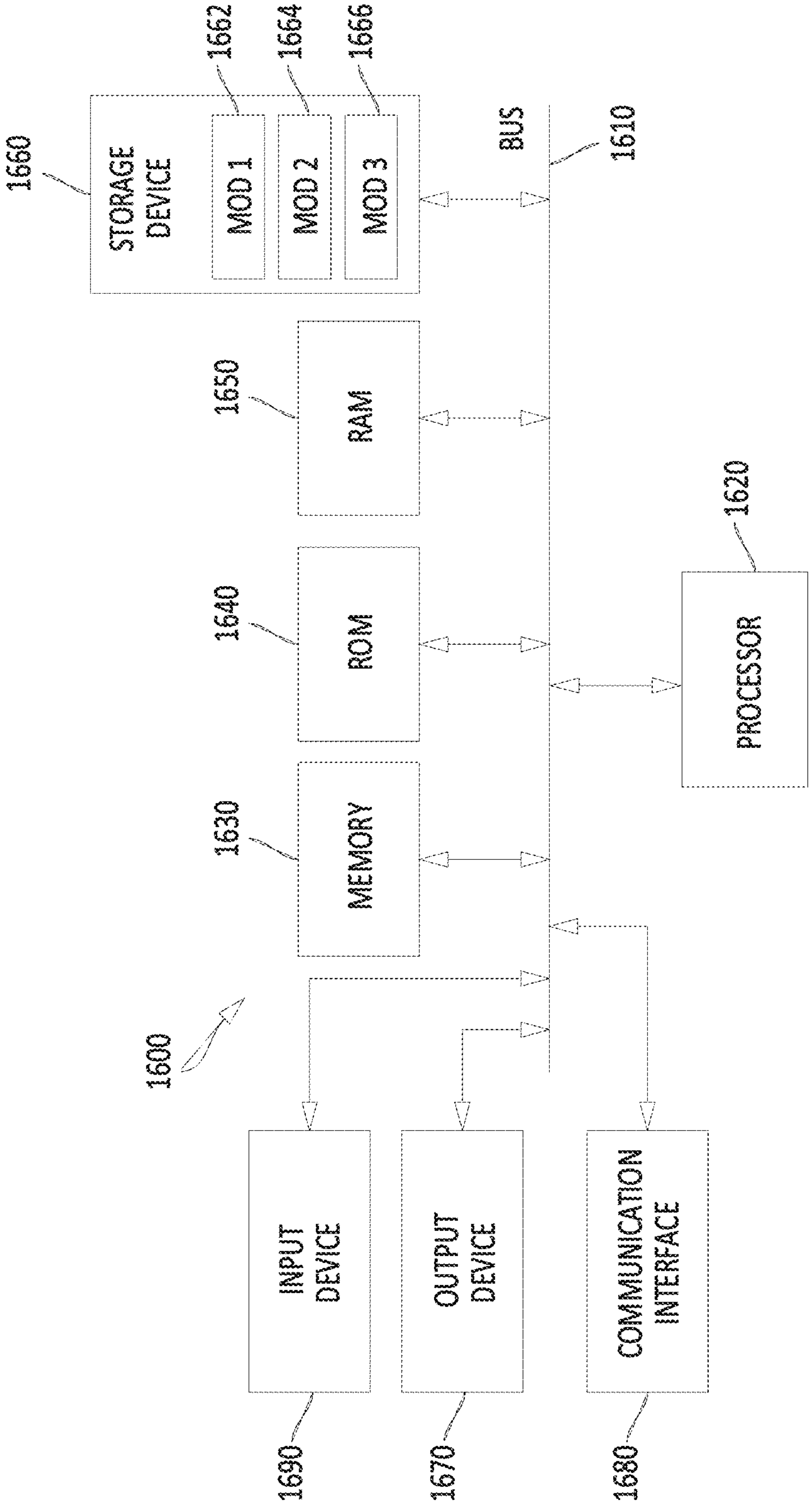
FIG. 11 shows an example of a computing system used in this study, according to an embodiment of the present invention.

With reference to FIG. 11, an exemplary system includes a general-purpose computing device 1600, including a processing unit (CPU or processor) 1620 and a system bus 1610 that couples various system components including the system memory 1630 such as read-only memory (ROM) 1640 and random-access memory (RAM) 1650 to the processor 1620. The system 1600 can include a cache of high-speed memory connected directly with, in close proximity to, or integrated as part of the processor 1620. The system 1600 copies data from the memory 1630 and/or the storage device 1660 to the cache for quick access by the processor 1620. In this way, the cache provides a performance boost that avoids processor 1620 delays while waiting for data. These and other modules can control or be configured to control the processor 1620 to perform various actions. Other system memory 1630 may be available for use as well. The memory 1630 can include multiple different types of memory with different performance characteristics. It can be appreciated that the disclosure may operate on a computing device 1600 with more than one processor 1620 or on a group or cluster of computing devices networked together to provide greater processing capability. The processor 1620 can include any general-purpose processor and a hardware module or software module, such as module 1 1662, module 2 1664, and module 3 1666 stored in storage device 1660, configured to control the processor 1620 as well as a special-purpose processor where software instructions are incorporated into the actual processor design. The processor 1620 may essentially be a completely self-contained computing system, containing multiple cores or processors, a bus, memory controller, cache, etc. A multi-core processor may be symmetric or asymmetric.

The system bus 1610 may be any of several types of bus structures including a memory bus or memory controller, a peripheral bus, and a local bus using any of a variety of bus architectures. A basic input/output (BIOS) stored in ROM 1640 or the like, may provide the basic routine that helps to transfer information between elements within the computing device 1600, such as during start-up. The computing device 1600 further includes storage devices 1660 such as a hard disk drive, a magnetic disk drive, an optical disk drive, tape drive or the like. The storage device 1660 can include software modules 1662, 1664, 1666 for controlling the processor 1620. Other hardware or software modules are contemplated. The storage device 1660 is connected to the system bus 1610 by a drive interface. The drives and the associated computer-readable storage media provide non-volatile storage of computer-readable instructions, data structures, program modules and other data for the computing device 1600. In one aspect, a hardware module that performs a particular function includes the software component stored in a tangible computer-readable storage medium in connection with the necessary hardware components, such as the processor 1620, bus 1610, display 1670, and so forth, to carry out the function. In another aspect, the system can use a processor and computer-readable storage medium to store instructions which, when executed by a processor (e.g., one or more processors), cause the processor to perform a method or other specific actions. The basic components and appropriate variations are contemplated depending on the type of device, such as whether the device 1600 is a small, handheld computing device, a desktop computer, or a computer server.

Although the exemplary embodiment described herein employs the hard disk 1660, other types of computer-readable media which can store data that are accessible by a computer, such as magnetic cassettes, flash memory cards, digital versatile disks, cartridges, random access memories (RAMs) 1650, and read-only memory (ROM) 1640, may also be used in the exemplary operating environment. Tangible computer-readable storage media, computer-readable storage devices, or computer-readable memory devices, expressly exclude media such as transitory waves, energy, carrier signals, electromagnetic waves, and signals per se.

To enable user interaction with the computing device 1600, an input device 1690 represents any number of input mechanisms, such as a microphone for speech, a touch-sensitive screen for gesture or graphical input, keyboard, mouse, motion input, speech and so forth. An output device 1670 can also be one or more of a number of output mechanisms known to those of skill in the art. In some instances, multimodal systems enable a user to provide multiple types of input to communicate with the computing device 1600. The communications interface 1680 generally governs and manages the user input and system output. There is no restriction on operating on any particular hardware arrangement and therefore the basic features here may easily be substituted for improved hardware or firmware arrangements as they are developed.

The technology discussed herein refers to computer-based systems and actions taken by, and information sent to and from, computer-based systems. One of ordinary skill in the art will recognize that the inherent flexibility of computer-based systems allows for a great variety of possible configurations, combinations, and divisions of tasks and functionality between and among components. For instance, processes discussed herein can be implemented using a single computing device or multiple computing devices working in combination. Databases, memory, instructions, and applications can be implemented on a single system or distributed across multiple systems. Distributed components can operate sequentially or in parallel.

Use of language such as “at least one of X, Y, and Z,” “at least one of X, Y, or Z,” “at least one or more of X, Y, and Z,” “at least one or more of X, Y, or Z,” “at least one or more of X, Y, and/or Z,” or “at least one of X, Y, and/or Z,” are intended to be inclusive of both a single item (e.g., just X, or just Y, or just Z) and multiple items (e.g., {X and Y}, {X and Z}, {Y and Z}, or {X, Y, and Z}). The phrase “at least one of” and similar phrases are not intended to convey a requirement that each possible item must be present, although each possible item may be present.

An aspect of the present invention is to provide a method for generating volumetric modulated arc therapy-computed tomography (VMAT-CT). The method includes receiving, at a computer system having at least one processor, electronic portal imaging device (EPID) images collected during VMAT; performing, via the at least one processor, Online Region-based Active Contour Method (ORACM) on the EPID images, resulting in binarized images; performing, via the at least one processor, multi-leaf collimator (MLC) motion modeling on the binarized images, resulting in motion modeled EPID images with most of blurred regions within the EPID images removed; performing, via the at least one processor, an outlier-filtering algorithm on the motion modeled EPID images, resulting in further filtered EPID images; executing, via the at least one processor, a conventional FDK-based VMAT-CT reconstruction algorithm on the further filtered EPID images to provide FDK-reconstructed images; executing, via the at least one processor, an iterative VMAT-CT reconstruction algorithm that combines compressed sensing and block matching and 3D filtering, on the FDK-reconstructed images, resulting in VMAT-CT images; and outputting the VMAT-CT images.

In an embodiment, the method further includes applying, via the at least one processor, a compressed sensing (CS)-based iterative reconstruction algorithm to further improve image quality of the EPID images after performing the multi-leaf collimator (MLC) motion modeling.

In an embodiment, performing, via the at least one processor, the multi-leaf collimator (MLC) motion modeling on the binarized images includes removing blurry edges within EPID images resulting in the motion modeled EPID images with most of the blurred regions within the EPID images removed.

In an embodiment, performing, via the at least one processor, the multi-leaf collimator (MLC) motion modeling on the binarized images includes securing data alignment between the EPID images and linear accelerator (LINAC) log file containing MLC positions, jaw positions, gantry angles, and cumulative monitor units.

In an embodiment, the method further includes interpolating, via the at least one processor, the LINAC log file into higher time resolution.

In an embodiment, performing, via the at least one processor, the outlier-filtering algorithm on the motion modeled EPID images includes performing the outlier-filtering algorithm before and after performing, via the at least one processor, a convolution of the EPID images with a lambda filter.

In an embodiment, the block matching and 3D filtering algorithm uses Wiener filtering.

In an embodiment, executing, via the at least one processor, the iterative VMAT-CT reconstruction algorithm that combines the compressed sensing and the block matching and the 3D filtering, on the FDK-reconstructed images includes performing, via the at least one processor, a total variation (TV) minimization resulting in VMAT-CT images.

In an embodiment, the executing, via the at least one processor, of the iterative VMAT-CT reconstruction algorithm that combines the compressed sensing and the block matching and the 3D filtering, on the FDK-reconstructed images further includes estimating, via the at least one processor, a denoised image using hard thresholding during a collaborative filtering, resulting in an estimated denoised image; and using an original noisy image and the estimated denoised image during the iterative VMAT-CT reconstruction algorithm.

In an embodiment, executing, via the at least one processor, the iterative VMAT-CT reconstruction algorithm is stopped if an iteration reaches a set maximum iteration number or if a square difference of reconstructions between two successive iterations is below a predetermined threshold.

An aspect of the present invention is to also provide a system for generating volumetric modulated arc therapy-computed tomography (VMAT-CT) implemented on a computer system having one or more processors. The computer system is configured: to receive electronic portal imaging device (EPID) images collected during VMAT; to perform Online Region-based Active Contour Method (ORACM) on the EPID images, resulting in binarized images; to perform multi-leaf collimator (MLC) motion modeling on the binarized images, resulting in motion modeled EPID images with most of blurred regions within the EPID images removed; to perform an outlier-filtering algorithm on the motion modeled EPID images, resulting in further filtered EPID images; to execute a conventional FDK-based VMAT-CT reconstruction algorithm on the further filtered EPID images to provide FDK-reconstructed images; to execute an iterative VMAT-CT reconstruction algorithm that combines compressed sensing and block matching and 3D filtering, on the FDK-reconstructed images, resulting in VMAT-CT images; and to output the VMAT-CT images.

In an embodiment, the computer system is configured to apply a compressed sensing (CS)-based iterative reconstruction algorithm to further improve image quality of the EPID images after performing the multi-leaf collimator (MLC) motion modeling.

In an embodiment, the computer system is configured to remove blurry edges within EPID images resulting in the motion modeled EPID images with most of the blurred regions within the EPID images removed.

In an embodiment, the computer system is configured to secure data alignment between the EPID images and linear accelerator (LINAC) log file containing MLC positions, jaw positions, gantry angles, and cumulative monitor units.

In an embodiment, the computer system is configured to interpolate the LINAC log file into higher time resolution.

In an embodiment, the computer system is configured perform the outlier-filtering algorithm before and after performing a convolution of the EPID images with a lambda filter.

In an embodiment, the block matching and 3D filtering algorithm uses Wiener filtering.

In an embodiment, the computer system is configured to perform a total variation (TV) minimization resulting in VMAT-CT images.

In an embodiment, the computer system is further configured to: estimate a denoised image using hard thresholding during a collaborative filtering; and using an original noisy image and the estimated denoised image during execution of the iterative VMAT-CT reconstruction algorithm.

In an embodiment, the computer system is configured to stop execution of the iterative VMAT-CT reconstruction algorithm if an iteration reaches a set maximum iteration number or if a square difference of reconstructions between two successive iterations is below a predetermined threshold.

Another aspect of the present invention is to provide a non-transitory computer-readable medium storing instructions that, when executed by a computer system having one or more processors, cause the computer system: to receive electronic portal imaging device (EPID) images collected during VMAT; to perform Online Region-based Active Contour Method (ORACM) on the EPID images, resulting in binarized images; to perform multi-leaf collimator (MLC) motion modeling on the binarized images, resulting in motion modeled EPID images with most of blurred regions within the EPID images removed; to perform an outlier-filtering algorithm on the motion modeled EPID images, resulting in further filtered EPID images; to execute a conventional FDK-based VMAT-CT reconstruction algorithm on the further filtered EPID images to provide FDK-reconstructed images; to execute an iterative VMAT-CT reconstruction algorithm that combines compressed sensing and block matching and 3D filtering, on the FDK-reconstructed images, resulting in VMAT-CT images; and to output the VMAT-CT images.

The various embodiments described above are provided by way of illustration only and should not be construed to limit the scope of the disclosure. Various modifications and changes may be made to the principles described herein without following the example embodiments and applications illustrated and described herein, and without departing from the spirit and scope of the disclosure. For example, unless otherwise explicitly indicated, the steps of a process or method may be performed in an order other than the example embodiments discussed above. Likewise, unless otherwise indicated, various components may be omitted, substituted, or arranged in a configuration other than the example embodiments discussed above.

While various embodiments of the present invention have been described above, it should be understood that they have been presented by way of example only, and not limitation. Thus, the breadth and scope of the present invention should not be limited by any of the above-described illustrative embodiments, or following examples, but should instead be defined only in accordance with the following claims and their equivalents.

The embodiments illustrated and discussed in this specification are intended only to teach those skilled in the art how to make and use the invention. In describing embodiments of the disclosure, specific terminology is employed for the sake of clarity. However, the disclosure is not intended to be limited to the specific terminology so selected. The above-described embodiments, and following examples, may be modified or varied, without departing from the invention, as appreciated by those skilled in the art in light of the above teachings. It is therefore to be understood that, within the scope of the claims and their equivalents, the invention may be practiced otherwise than as specifically described. For example, it is to be understood that the present disclosure contemplates that, to the extent possible, one or more features of any embodiment can be combined with one or more features of any other embodiment.

I claim:

1. A method for generating volumetric modulated arc therapy-computed tomography (VMAT-CT) comprising:

receiving, at a computer system comprising at least one processor, electronic portal imaging device (EPID) images collected during VMAT;

performing, via the at least one processor, Online Region-based Active Contour Method (ORACM) on the EPID images, resulting in binarized images;

performing, via the at least one processor, multi-leaf collimator (MLC) motion modeling on the binarized images, resulting in motion modeled EPID images with most of blurred regions within the EPID images removed;

performing, via the at least one processor, an outlier-filtering algorithm on the motion modeled EPID images, resulting in further filtered EPID images;

executing, via the at least one processor, a conventional FDK-based VMAT-CT reconstruction algorithm on the further filtered EPID images to provide FDK-reconstructed images;

executing, via the at least one processor, an iterative VMAT-CT reconstruction algorithm that combines compressed sensing and block matching and 3D filtering, on the FDK-reconstructed images, resulting in VMAT-CT images; and outputting the VMAT-CT images.

2. The method according to claim 1, further comprising applying, via the at least one processor, a compressed sensing (CS)-based iterative reconstruction algorithm to further improve image quality of the EPID images after performing the multi-leaf collimator (MLC) motion modeling.

3. The method according to claim 1, wherein performing, via the at least one processor, the multi-leaf collimator (MLC) motion modeling on the binarized images comprises removing blurry edges within EPID images resulting in the motion modeled EPID images with most of the blurred regions within the EPID images removed.

4. The method according to claim 1, wherein performing, via the at least one processor, the multi-leaf collimator (MLC) motion modeling on the binarized images comprises securing data alignment between the EPID images and linear accelerator (LINAC) log file containing MLC positions, jaw positions, gantry angles, and cumulative monitor units.

5. The method according to claim 4, further comprising interpolating, via the at least one processor, the LINAC log file into higher time resolution.

6. The method according to claim 1, wherein performing, via the at least one processor, the outlier-filtering algorithm on the motion modeled EPID images comprises performing the outlier-filtering algorithm before and after performing, via the at least one processor, a convolution of the EPID images with a lambda filter.

7. The method according to claim 1, wherein the block matching and 3D filtering algorithm uses Wiener filtering.

8. The method according to claim 1, wherein executing, via the at least one processor, the iterative VMAT-CT reconstruction algorithm that combines the compressed sensing and the block matching and the 3D filtering, on the FDK-reconstructed images comprises performing, via the at least one processor, a total variation (TV) minimization resulting in VMAT-CT images.

9. The method according to claim 1, wherein the executing, via the at least one processor, of the iterative VMAT-CT reconstruction algorithm that combines the compressed sensing and the block matching and the 3D filtering, on the FDK-reconstructed images further comprises:

estimating, via the at least one processor, a denoised image using hard thresholding during a collaborative filtering, resulting in an estimated denoised image; and using an original noisy image and the estimated denoised image during the iterative VMAT-CT reconstruction algorithm.

10. The method according to claim 1, wherein executing, via the at least one processor, the iterative VMAT-CT reconstruction algorithm is stopped if an iteration reaches a set maximum iteration number or if a square difference of reconstructions between two successive iterations is below a predetermined threshold.

11. A system for generating volumetric modulated arc therapy-computed tomography (VMAT-CT) implemented on a computer system having one or more processors, the computer system being configured:

to receive electronic portal imaging device (EPID) images collected during VMAT;

to perform Online Region-based Active Contour Method (ORACM) on the EPID images, resulting in binarized images;

to perform multi-leaf collimator (MLC) motion modeling on the binarized images, resulting in motion modeled EPID images with most of blurred regions within the EPID images removed;

to perform an outlier-filtering algorithm on the motion modeled EPID images, resulting in further filtered EPID images;

to execute a conventional FDK-based VMAT-CT reconstruction algorithm on the further filtered EPID images to provide FDK-reconstructed images;

to execute an iterative VMAT-CT reconstruction algorithm that combines compressed sensing and block matching and 3D filtering, on the FDK-reconstructed images, resulting in VMAT-CT images; and to output the VMAT-CT images.

12. The system according to claim 11, wherein the computer system is configured to apply a compressed sensing (CS)-based iterative reconstruction algorithm to further improve image quality of the EPID images after performing the multi-leaf collimator (MLC) motion modeling.

13. The system according to claim 11, wherein the computer system is configured to remove blurry edges within EPID images resulting in the motion modeled EPID images with most of the blurred regions within the EPID images removed.

14. The system according to claim 11, wherein the computer system is configured to secure data alignment between the EPID images and linear accelerator (LINAC) log file containing MLC positions, jaw positions, gantry angles, and cumulative monitor units.

15. The system according to claim 14, wherein the computer system is configured to interpolate the LINAC log file into higher time resolution.

16. The system according to claim 11, wherein the computer system is configured perform the outlier-filtering algorithm before and after performing a convolution of the EPID images with a lambda filter.

17. The system according to claim 11, wherein the block matching and 3D filtering algorithm uses Wiener filtering.

18. The system according to claim 11, wherein the computer system is configured to perform a total variation (TV) minimization resulting in VMAT-CT images.

19. The system according to claim 11, wherein the computer system is further configured to:

estimate a denoised image using hard thresholding during a collaborative filtering; and using an original noisy image and the estimated denoised image during execution of the iterative VMAT-CT reconstruction algorithm.

20. The system according to claim 11, wherein the computer system is configured to stop execution of the iterative VMAT-CT reconstruction algorithm if an iteration reaches a set maximum iteration number or if a square difference of reconstructions between two successive iterations is below a predetermined threshold.

21. A non-transitory computer-readable medium storing instructions that, when executed by a computer system having one or more processors, cause the computer system:

to receive electronic portal imaging device (EPID) images collected during VMAT;

to perform Online Region-based Active Contour Method (ORACM) on the EPID images, resulting in binarized images;

to perform multi-leaf collimator (MLC) motion modeling on the binarized images, resulting in motion modeled EPID images with most of blurred regions within the EPID images removed;

to perform an outlier-filtering algorithm on the motion modeled EPID images, resulting in further filtered EPID images;

to execute a conventional FDK-based VMAT-CT reconstruction algorithm on the further filtered EPID images to provide FDK-reconstructed images;

to execute an iterative VMAT-CT reconstruction algorithm that combines compressed sensing and block matching and 3D filtering, on the FDK-reconstructed images, resulting in VMAT-CT images; and to output the VMAT-CT images.

* * * * *